US008210169B2

(12) United States Patent
Ahlmén et al.

(10) Patent No.: US 8,210,169 B2
(45) Date of Patent: Jul. 3, 2012

(54) DOSING SAFETY ARRANGEMENT IN A DELIVERY APPARATUS FOR PRESSURIZED MEDICAL LIQUIDS

(75) Inventors: Christer Ahlmén, Sollentuna (SE); Mario Loncar, Ekerö (SE)

(73) Assignee: Maquet Critical Care AB, Solna (SE)

( * ) Notice: Subject to any disclaimer, the term of this patent is extended or adjusted under 35 U.S.C. 154(b) by 972 days.

(21) Appl. No.: 11/995,167

(22) PCT Filed: Jul. 14, 2005

(86) PCT No.: PCT/EP2005/053379
§ 371 (c)(1),
(2), (4) Date: Jan. 9, 2008

(87) PCT Pub. No.: WO2007/006348
PCT Pub. Date: Jan. 18, 2007

(65) Prior Publication Data
US 2009/0165787 A1 Jul. 2, 2009

(51) Int. Cl.
*A61M 15/00* (2006.01)
*A61M 16/10* (2006.01)
*A61M 16/00* (2006.01)
*A62B 9/02* (2006.01)

(52) U.S. Cl. ......... 128/203.14; 128/203.12; 128/203.15; 128/200.24; 128/205.24; 128/204.21; 128/204.18

(58) Field of Classification Search .......... 128/200.11–200.23, 200.24, 203.12, 128/203.15, 203.16, 203.17, 203.25, 203.26, 128/203.27, 204.14, 204.17, 204.18, 204.21; 239/338, 102.1, 102.2; 261/DIG. 65, 129, 261/154; 122/4 A, 5.5 A, 7 B, 13.01, 13.3–19.2, 122/33, 487, DIG. 7; 604/93.01, 131, 132, 604/133, 134, 135, 140, 141, 143, 146, 147, 604/151, 152, 207, 208, 212, 213, 214, 215, 604/218, 246, 248, 257
See application file for complete search history.

(56) References Cited

U.S. PATENT DOCUMENTS

| 4,152,379 A * | 5/1979 | Suhr .............................. 261/142 |
| 4,172,105 A * | 10/1979 | Miller et al. .................... 261/66 |
| 4,366,105 A * | 12/1982 | Nowacki ......................... 261/35 |
| 4,500,480 A * | 2/1985 | Cambio, Jr. .................. 261/104 |
| 4,722,334 A * | 2/1988 | Blackmer et al. ........ 128/203.16 |
| 4,750,483 A * | 6/1988 | Ankartross et al. ...... 128/203.26 |
| 5,049,317 A * | 9/1991 | Kiske et al. .................... 261/16 |
| 5,243,973 A | 9/1993 | Falb et al. |
| 5,645,052 A * | 7/1997 | Kersey ..................... 128/203.26 |
| 5,730,119 A * | 3/1998 | Lekholm .................. 128/200.24 |

(Continued)

FOREIGN PATENT DOCUMENTS

| EP | 0 710 489 A2 | 5/1996 |
| EP | 1 064 962 A1 | 1/2001 |
| EP | 1 300 172 A1 | 4/2003 |
| WO | WO2007/000190 | 1/2007 |

(Continued)

*Primary Examiner* — Annette Dixon
(74) *Attorney, Agent, or Firm* — Schiff Hardin LLP

(57) ABSTRACT

A delivery apparatus for pressurized medical liquids has a primary reservoir that pressurizes a medical liquid therein to a driving pressure, a second reservoir having an inlet connected to receive pressurized liquid from the primary reservoir via a controllable intermediate valve, and an outlet for discharge of the received medical liquid via a controllable dosing valve. A pressure measuring unit measures the pressure in the secondary reservoir and a control unit controls the intermediate valve and the dosing valve by monitoring the operation of the intermediate valve and the dosing valve dependent on the measured pressure value from the pressure measuring unit. The control unit generates a status signal dependent on predetermined rules for measured pressure changes compared with calculated pressure changes.

10 Claims, 1 Drawing Sheet

U.S. PATENT DOCUMENTS

| | | | | |
|---|---|---|---|---|
| 5,967,141 A * | 10/1999 | Heinonen | | 128/203.12 |
| 6,289,891 B1 | 9/2001 | Cewers | | |
| 6,739,288 B1 * | 5/2004 | Kumamoto | | 122/15.1 |
| 6,766,835 B1 * | 7/2004 | Fima | | 141/95 |
| 7,017,528 B2 * | 3/2006 | Kumamoto | | 122/15.1 |
| 7,032,595 B2 * | 4/2006 | Bunke et al. | | 128/203.25 |
| 7,316,204 B2 * | 1/2008 | Kumamoto | | 122/15.1 |
| 7,316,205 B2 * | 1/2008 | Kumamoto | | 122/15.1 |
| 7,415,942 B2 * | 8/2008 | Kumamoto | | 122/15.1 |
| 2002/0069876 A1 | 6/2002 | Loser et al. | | |
| 2003/0079745 A1 | 5/2003 | Bunke et al. | | |

* cited by examiner

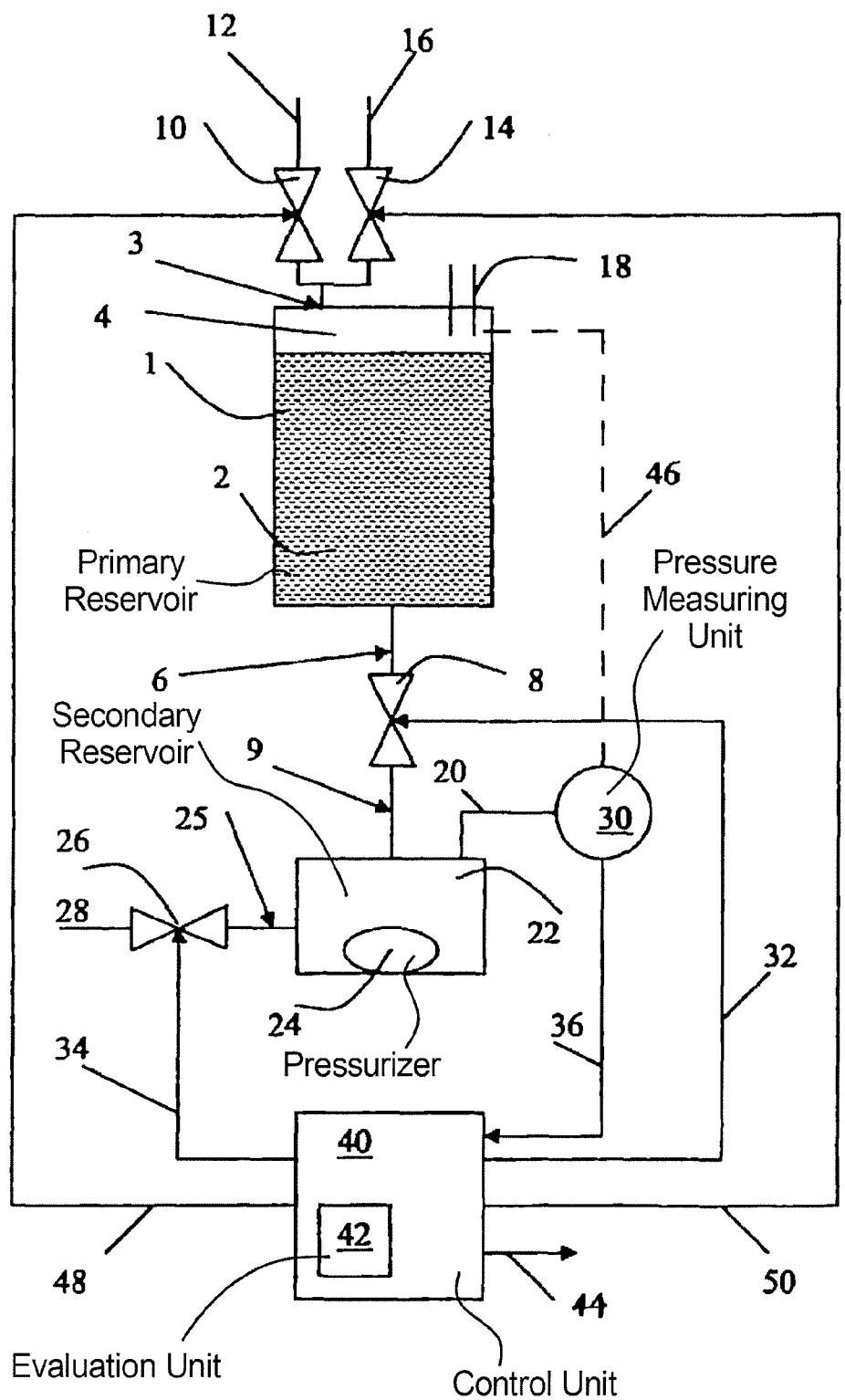

DOSING SAFETY ARRANGEMENT IN A DELIVERY APPARATUS FOR PRESSURIZED MEDICAL LIQUIDS

FIELD OF THE INVENTION

The present invention relates in general to delivery apparatuses for pressurized medical liquids and in particular to a dosing safety arrangement in such a delivery apparatus.

DESCRIPTION OF THE PRIOR ART

In delivery apparatuses for pressurized medical liquids it is known to maintain a medical liquid in a reservoir at a delivery pressure by means of pressurized gas. The gas is inlet to the reservoir from a pressurized gas source. In the reservoir the gas exerts its pressure on the medical liquid and the pressurized liquid is delivered through a controllable outlet. Such an apparatus is used for example in a vaporizer for liquid anesthetic wherein a delivery apparatus delivers doses of the liquid via a controllable outlet valve and an injector coupled to the outlet and into a flow of breathing gas. In this kind of use it is important that the delivery apparatus is capable of delivering doses with a certain volume of liquid with a high degree of safety.

The basic idea for a delivery apparatus of this kind is that the delivered volume of liquid shall be dependent only on the differential pressure over the controllable outlet and on the time during which the outlet is open. However, in practical use there is a risk that the dosed amount deviates from the intended dose due to malfunction of the controllable outlet valve. There is also a risk that large amounts of medical liquid leak out in case of a breakdown of the controllable outlet valve. There is a need for reducing these risks and the extent of the consequences of such a malfunction or breakdown in order to improve patient safety.

EP 1 300 172 discloses a delivery apparatus for pressurized liquid anesthetics. In this piece of prior art a primary reservoir is devised with primary pressurizer in order to pressurise the liquid to a delivery pressure basically as described in the background section above. The primary reservoir in its turn is connected to a secondary reservoir so as to deliver pressurized liquid to the secondary reservoir. The secondary reservoir is provided with an outlet for discharge of medical liquid and with a secondary pressurizer devised to supply compensating pressure to the liquid in the secondary reservoir in order to maintain it at the delivery pressure when liquid is discharged from the reservoir. A valve is provided between the primary reservoir and the secondary reservoir in order to avoid flow back from the secondary reservoir to the primary reservoir when delivery pressure is removed from the primary reservoir. The purpose is to be able to temporarily allow interruption of the pressurizing activity in the primary reservoir without interruption of delivery of the pressurized liquid from the secondary reservoir. Thereby the primary reservoir can be refilled at atmospheric pressure during operation of the delivery apparatus. This prior art does not solve the above problem nor provide a solution with regard to reduction of the risk and the extent of the consequences of leakage due to a breakdown of the controllable outlet valve.

United States Patent Application Publication No. 2003/0079745 A1 discloses a device for metering anesthetic. This prior art is directed to the problem of making new anesthetic immediately available for metering after change of anesthetic. There is a primary and a secondary reservoir, herein called intermediate container, for the anesthetic as well as a pressure-measuring means for measuring the pressure in the secondary reservoir. The measured pressure is used for monitoring the metering pressure as well as for calculation of the volume of anesthetic metered for correction purposes.

SUMMARY OF THE INVENTION

An object of the present invention is to improve the safety with regard to unintentional excessive dosing of medical liquid into a breathing gas from a delivery apparatus for pressurized medical liquids.

According to the present invention the problem is solved by a device that monitors the function and operation of a dosing valve and limits the amount of fluid that can leak out in case of a breakdown of the dosing valve. A primary reservoir housing the main storage of medical liquid is pressurized and feeds medical liquid via a controllable intermediate valve to a secondary reservoir housing a smaller amount of medical liquid. The secondary reservoir has a separate pressurizer that maintains the pressure at a suitable delivery pressure and a dosing valve for discharge of medical liquid for example into a stream of breathing gas in an anesthetic system. During discharge of medical liquid from the secondary valve the controllable intermediate valve between the primary reservoir and the secondary reservoir is closed and the maximum possible amount that can leak out is delimited to the volume in the secondary reservoir.

The function and operation of the dosing valve is monitored by repeatedly measuring the pressure in the secondary reservoir and comparing any pressure change with the expected pressure change based on the volume of the discharged dose of medical liquid. This expected pressure change can be calculated or determined by experiment. The calculation is based on the total liquid volume in the secondary reservoir, the pressure before discharge of the medical dose and the specifics of the pressurizer in the secondary reservoir. If the pressure change mismatches the discharged dose of medical liquid, it is concluded that the dosing valve or its control means is defect. By monitoring the pressure in the secondary reservoir also the function of the intermediate valve can be monitored. Various alarm signals or activation signals can be generated dependent on predetermined rules.

The invention further has the advantage that dosing and discharge of medical liquid from the secondary reservoir can continue uninterrupted for a period of time also when the primary reservoir is depressurized. This is useful for example when the primary reservoir is refilled under atmospheric pressure for example from a separate container.

BRIEF DESCRIPTION OF THE DRAWINGS

The FIGURE schematically shows a delivery apparatus with two reservoirs in accordance with an embodiment of the invention.

DESCRIPTION OF THE PREFERRED EMBODIMENTS

The FIGURE shows schematically the invention applied in a delivery apparatus for pressurized medical liquids. A primary reservoir 1 for a main storage of medical liquid 2 is provided with a primary pressurizer which in the shown embodiment operates with pressurized gas. The primary reservoir is for this purpose in its upper part provided with an inlet 3 for pressurized gas that is controllably inlet through a gas inlet valve 10 from a source 12 of pressurized gas. The pressurized gas gathers in the space 4 above the liquid surface and exerts pressure on the liquid surface thereby pressurizing the liquid to a driving pressure or a delivery pressure. The inlet 3 is also used for controllable evacuation of gas from the reservoir through a gas outlet valve 14 to a gas evacuation system 16. The primary reservoir 1 is in its lower part provided with an outlet 6 for communication of pressurized medical liquid via a controllable intermediate valve 8 to a secondary reservoir 22. The primary reservoir 1 is further in its upper part provided with a refill inlet 18 provided for refilling the reservoir with medical liquid. The refill inlet is only schematically drawn but would typically be provided with a re-sealable port that can be opened to refill medical liquid preferably under about atmospheric pressure and sealed to withstand the pressurizing pressure from the gas during operation.

The secondary reservoir 22 is thus at an inlet 9 connected to the controllable intermediate valve 8 for receiving pressurized medical liquid from the primary reservoir 1. A secondary pressurizer 24 is provided to maintain the pressure in the secondary reservoir when the intermediate valve 8 is closed and no pressurizing gas pressure is received from the primary reservoir. In the shown embodiment, the secondary pressure means is formed by means of a body that has elastic walls and contains a compressible medium such as a gas. The walls of the thus elastic body is in one embodiment made of a metal membrane or some other non-porous material in order to prevent diffusion of the medical fluid through the walls of the body and leakage out of the pressurized body. It is within the scope of the invention that the secondary pressurizer can be implemented in other ways, for example as disclosed in the two prior art documents cited above. For discharge of medical liquid there is an outlet 25 from the secondary reservoir that is coupled to a controllable dosing valve 26. The dosing valve 26 is in its turn connected to an injector nozzle 28 for delivering doses of pressurized medical liquid into a flow of breathing gas.

A pressure measuring unit 30 is by a secondary pressure input line 20 to the secondary reservoir 22 for measuring the pressure of its content of medical liquid. An output pressure value signal line 36 of the pressure measuring unit 30 is coupled to a control unit 40 to communicate a parameter value in the form of a pressure value signal. The control unit 40 is with an output refill signal line 32 coupled to the intermediate valve 8 for controlling its closing and opening, and thereby controlling the refilling and pressurizing of the secondary reservoir with medical liquid from the primary reservoir 1. Similarly, the control unit 40 is with an output dosing signal line 34 coupled to the delivery valve 26 for controlling its opening and closing, and thereby controlling the discharge of doses of medical liquid from the secondary reservoir 22. The valves 8 and 26 are in different embodiments pneumatically or electrically controlled. The control unit 40 is provided with an evaluation unit 42 that is configured to evaluate input parameter values, such as the mentioned pressure value and possibly other parameter values, in relation to predetermined rules or values. A status signal output 44 is provided in the control unit 40 for communicating status information of the delivery apparatus to an operator or to other devices. For example, the status signal output 44 may be communicated to an alarm unit 43 for activating an alarm in case of malfunction of the delivery apparatus. Different kinds of alarm signals or activation signals may be provided dependent on the status signal and on a predetermined scheme or rules. The activation signals are provided for and configured to activate a selected function of the delivery apparatus, for example to close a valve in order to stop leakage, or to open other valves to depressurize the secondary reservoir.

In operation of the delivery apparatus, the primary reservoir 1 filled with medical liquid is pressurized by opening the inlet valve 10 thus allowing pressurizing gas from gas source 12 into the primary reservoir 1. The intermediate valve 8 is opened in response to an actuating refill control signal from the control unit 40 communicated via the refill signal line 32, thereby allowing medical liquid to pass from the primary reservoir and be received in the secondary reservoir 22 and simultaneously pressurizing the content of the secondary reservoir. The pressure in the secondary reservoir 22 is regularly and with a predetermined frequency measured by the pressure measuring unit 30 and current pressure value signals are communicated to the control unit 40. Doses of medical liquid are discharged from the secondary reservoir 22 via the outlet 25 by opening the dosing valve 26 in response to a dosing control signal from the control unit 40 communicated via the dosing signal line 34. Preferably, the discharge of medical liquid is carried out by opening the dosing valve in pulses and measuring the current pressure after each pulse with the dosing valve. The pressure change after each pulse is determined and the pressure change is compared with an expected pressure change due to the intended amount of discharged medical liquid by the evaluation unit 42. The intended amount of discharged medical liquid is determined in accordance with a predetermined algorithm dependent on the pressure in the secondary reservoir and on known characteristics of the dosing valve 26 and its opening time during each pulse. A corresponding expected pressure change is calculated dependent on the determined amount of discharged medical liquid. If the pressure change is too small or too large in relation to the intended amount of discharged medical liquid and the pressure drop expected for said amount of discharged liquid, it is concluded that the dosing valve 26 or the control of the valve is defect. Similarly, if there is a too small pressure drop or none at all after an actuation of the dosing valve 26, it is concluded that either the intermediate valve 8 or the dosing valve 26 is defect. In case a pressure drop is determined although the dosing valve 26 has not been actuated it is concluded that there is a leakage from the secondary reservoir 22, possibly through the dosing valve 26. Status signals are generated by the control unit dependent on the concluded status of the delivery apparatus. Advantageously, threshold values T1 or T2 could be introduced to decide if the deviation of the measured pressure from the expected pressure is such that a status signal or activation signals should be generated.

The measured pressure values are also used to determine the actually discharged amount of medical liquid from the secondary reservoir 22. The actually discharged amount is calculated dependent on the pressure change after actuation of the dosing valve 26 and on known characteristics of the dosing valve 26. The evaluation means is in one embodiment configured to compare and evaluate the relation between intended dose and actually discharged dose. The invention thus enables cross-checking the discharged doses of medical liquid as well as monitoring the dosing and intermediate valves. The invention also limits the possible leakage of medical liquid in case of breakdown of the dosing valve 26. When a defect in the dosing valve 26 is detected, the primary reservoir 1 and the secondary reservoir 22 are depressurized by closing the gas inlet valve 10, and by opening the gas outlet valve 14 and the intermediate valve 8 for a period of time. The intermediate valve 8 is closed again, and thereafter only the amount of medical liquid that is present in the secondary reservoir 22, in the dosing valve 26 and in possible tubing there between can leak out into the breathing system. To achieve that, the control unit 40 will in that case generate activation signals which via signal lines 32, 48 and 50 open and close the valves 8, 10 and 14 accordingly. The intermediate valve 8 between the primary reservoir and the secondary reservoir is monitored as mentioned above by checking for an expected pressure drop in connection with delivery of doses from the secondary reservoir.

In the embodiment with a secondary pressurizer 24 in the form of a compressible body or similar pressurizer that stores a limited amount of pressurizing energy, the pressure in the secondary reservoir 22 will decrease dependent on the amount of discharged medical liquid. Thereby also the flow rate through the dosing valve 26 will decrease and a decreasing amount of medical liquid will pass per time unit of dosing valve opening time. In order to discharge a certain dose, the required opening time or number of pulsed openings of the dosing valve 26 is calculated dependent on the current pressure in the secondary reservoir.

The pressure in the secondary reservoir is in one variety of the invention measured in relation to atmospheric pressure. In another variety, the pressure is measured as a differential pressure between the primary reservoir 1 and the secondary reservoir 22. For this optional purpose the pressure measuring means 30 also has a primary pressure input line 46 connected to the primary reservoir, as is schematically shown by the intermittently drawn line in FIG. 1. This alternative allows a more accurate measurement of the pressure decrease due to dosing and discharge of medical liquid. The differential pressure measurement configuration also enables measurement of the liquid level in the primary reservoir when the intermediary valve 8 is open and the dosing valve 26 is closed. Measured pressure difference is then the pressure from the liquid column in the primary reservoir, and the liquid level can be calculated dependent on the pressure difference and on the density of the medical liquid in a per se known manner.

The delivery apparatus in accordance with the present invention may advantageously be provided with a diffusion barrier in accordance with the co-pending application PCT/EP2005/053068.

Although modifications and changes may be suggested by those skilled in the art, it is the intention of the inventors to embody within the patent warranted heron all changes and modifications as reasonably and properly come within the scope of their contribution to the art.

The invention claimed is:

1. A delivery apparatus for pressurized medical liquids comprising:
    a primary reservoir and a primary pressurizer that pressurizes medical liquid in the primary reservoir to a driving pressure;
    a secondary reservoir having an inlet connected to receive pressurized liquid from the primary reservoir via a controllable intermediate valve, and a secondary pressurizer that supplies a maintaining pressure to the received pressurized liquid to maintain the pressurized liquid at substantially the delivered pressure, and an outlet for discharge of the received medical liquid via a controllable dosing valve adapted to communicate with a patient to supply said medical liquid to the patient;
    a pressure measuring unit that measures the pressure in the secondary reservoir;
    a control unit that controls the intermediate valve and that controls the dosing valve to open the dosing valve to permit a controlled discharged of said received medical liquid from said outlet to the patient;
    said control unit monitoring operation of the intermediate valve and the dosing valve dependent on measured pressure values from the pressure measuring unit and generating a status signal dependent on predetermined rules for measured pressure changes compared with calculated pressure changes; and
    said control unit being configured to automatically determine, from said measured pressure values, when refilling of said secondary reservoir is needed and to thereupon open said intermediate valve to refill said the secondary reservoir, but to always maintain said intermediate valve closed when said dosing valve is open in order to prevent an uncontrolled discharge of said medical liquid to the patient via the open dosing valve; thereby, improving the safety of the delivery apparatus.

2. The delivery apparatus of claim 1, wherein said control unit generates an alarm signal dependent on the status signal.

3. The delivery apparatus of claim 1, wherein said control unit generates an activation signal for activating a selected function of the delivery apparatus dependent on the status signal.

4. The delivery apparatus of claim 1, wherein said control unit determines the pressure change in the secondary reservoir regularly with a predetermined frequency.

5. The delivery apparatus of claim 1, wherein said control unit determines the pressure change in the secondary reservoir after each discharge of medical liquid from said secondary reservoir.

6. The delivery apparatus of claim 1, wherein said control unit, if the pressure change is smaller than a predetermined threshold value, generates a status signal that indicates that the dosing valve or the intermediate valve is defective.

7. The delivery apparatus of claim 1, wherein said control unit, if the pressure change is larger than a predetermined threshold value, generates a status signal that indicates that the dosing valve is defective.

8. The delivery apparatus of claim 7 comprising an evacuation valve connected to said primary reservoir, and wherein said control unit, in response to said status signal that indicates that the dosing valve is defective, is configured to open said evacuation valve and the intermediate valve to depressurize both said primary reservoir and said secondary reservoir and, when said pressure measuring unit indicates atmospheric pressure in said primary reservoir and in said secondary reservoir, to close the intermediate valve.

9. The delivery apparatus of claim 1, wherein said control unit, if there is a pressure decrease although the dosing valve has not been actuated, generates a status signal that indicates that there is a leakage from the secondary reservoir.

10. The delivery apparatus of claim 1, wherein the secondary pressurizer is a body with elastic walls and containing a compressible medium.

* * * * *